United States Patent [19]

Bhattacharya

[11] 4,092,229

[45] May 30, 1978

[54] THERMAL CONVECTION COUNTER STREAMING SEDIMENTATION AND FORCED CONVECTION GALVANIZATION METHOD FOR CONTROLLING THE SEX OF MAMMALIAN OFFSPRING

[76] Inventor: Bhairab C. Bhattacharya, 5016 S. 87th St., Omaha, Nebr. 68127

[21] Appl. No.: 734,243

[22] Filed: Oct. 20, 1976

Related U.S. Application Data

[60] Continuation-in-part of Ser. No. 641,501, Dec. 17, 1975, which is a division of Ser. No. 526,378, Nov. 22, 1974, Pat. No. 3,976,197.

[51] Int. Cl.$^2$ .......................................... G01N 27/26
[52] U.S. Cl. ............................... 204/180 R; 128/1 R; 195/1.8; 204/299 R; 209/11; 209/173
[58] Field of Search ................... 128/1 R; 204/180 R, 204/180 G, 299; 210/70, 71; 195/1.8; 209/11, 173

[56] References Cited

U.S. PATENT DOCUMENTS

| | | | |
|---|---|---|---|
| 2,247,065 | 6/1941 | Pauli et al. ........................ 204/180 R |
| 2,535,395 | 12/1950 | Dinsley ......................... 204/180 R X |
| 2,878,178 | 3/1959 | Bier ................................. 204/180 R |
| 2,944,541 | 7/1960 | Sacchi et al. ......................... 128/1 R |
| 3,135,816 | 6/1964 | Ram et al. .................... 204/180 R X |
| 3,413,208 | 11/1968 | Barg, Jr. et al. ................. 204/180 R |
| 3,687,806 | 8/1972 | Van den Bovenkamp ......... 128/1 R |
| 3,894,529 | 7/1975 | Shrimpton ............................ 128/1 R |
| 3,906,929 | 9/1975 | Augspurger ...................... 195/1.8 X |
| 4,009,260 | 2/1977 | Ericsson ........................... 195/1.8 X |

*Primary Examiner*—Arthur C. Prescott
*Attorney, Agent, or Firm*—Bacon & Thomas

[57] ABSTRACT

A method and apparatus for controlling the sex of mammalian offspring by separation of the X-chromosome female producing sperm and Y-chromosome male producing sperm according to their different characteristics of density of the respective cells and electric potential on the respective cell surfaces. Separation is accomplished by first producing a thermal convection counter stream within a sedimentation column containing a universal medium with sperm suspended therein and allowing the two sperm populations to settle into different fractions according to different densities. Subsequently, the fractions are further separated and concentrated utilizing convection galvanization. The positive and negative geotaxis applied to the sperm during thermal convection sedimentation in combination with galvanic forces applied during the convection galvanization facilitate a more efficient separation than previously obtained. This is due to the fact that a greater degree of separation of X and Y sperm is achieved by subjecting an unbalanced population of sperm cells, i.e., one predominating in X or Y cells, to convection galvanization. Thermal convection counter streaming sedimentation has been found to be a preferred method for attaining this unbalanced sperm population. The apparatus used to accomplish the above separation includes means for producing a temperature differential between axial and peripheral portions of the medium contained in the sedimentation column, thus creating the necessary thermal convection counter stream, as well as an electrophoreses cell comprising a convection column disposed between the two electrodes of the cell. Alternatively, the sedimentation apparatus and the convection galvanization apparatus may be combined. Additionally, the apparatus may comprise a laser capable of scanning the length of the thermal convection sedimentation column as well as laser detecting means to determine the distribution of sperm produced within the medium therein.

21 Claims, 4 Drawing Figures

STAGES OF DISTRIBUTION OF MALE AND FEMALE SPERM

THERMAL CONVECTION COUNTER STREAMING SEDIMENTATION AND FORCED CONVECTION GALVANIZATION METHOD FOR CONTROLLING THE SEX OF MAMMALIAN OFFSPRING

CROSS REFERENCE TO RELATED APPLICATIONS

This application is a continuation-in-part of application Ser. No. 641,501, filed Dec. 17, 1975 in the name of Bhairab C. Bhattacharya which is in turn a division of application Ser. No. 526,378 filed Nov. 22, 1974 by the same inventor, now U.S. Pat. No. 3,976,197.

Reference is made to the applications of Bhairab Chandra Bhattacharya, Ser. No. 443,473 filed Mar. 29, 1965 and now abandoned; Ser. No. 873,795 filed Nov. 4, 1969 by the same inventor, now U.S. Pat. No. 3,692,897, incorporated herein by reference; and application Ser. No. 336,454 filed Feb. 28, 1973 by the same inventor, now U.S. Pat. No. 3,816,249, also incorporated herein by reference.

BACKGROUND OF THE INVENTION

The present invention relates to a method and apparatus for controlling the sex of mammalian offspring by separation of X-chromosome female producing sperm of a certain density and electric potential from Y-chromosome male producing sperm of a differing density and electric potential.

As discussed in the aforementioned applications, the sex of offspring is controlled by the chromosomes of the particular sperm cell which fertilizes the egg. As further disclosed therein, X-chromosome-containing sperm which are responsible for producing female offspring are somewhat more dense than Y-chromosome-containing sperm which are responsible for producing male offspring. Additionally, it has been determined that X and Y-chromosome-containing sperm have a differing electric potential on their respective cell surfaces. These differences in density and electric potential make possible the separation of sperm into fractions containing substantially all of either the X or the Y sperm. Separation techniques utilizing these density and electric potential differences are suitable for use with all mammals including human beings and other primates, cattle, swine, sheep, rabbits, cats, dogs, goats, horses, donkeys, buffalo, etc. As previously disclosed, primarily in application Ser. No. 443,473, the method of separation by density has been to apply a buoyant force to the sperm to cause the more buoyant sperm to attain a different level in the separation medium than the less buoyant sperm where the buoyant force applied has been either positive or negative or both. As previously practiced, the separation of X and Y sperm cells by differing electric potential has been difficult due to the fact that while in the seminal fluid the positive and negative zeta potential of the female and male spermatozoa create an equilibrium within the dielectric constant of the medium thus making it difficult to draw them apart in a galvanic field. This equilibrium has been mainly due to the substantially equal populations of X and Y cells of opposite charge which have been subjected to this process. While various types of electrophoreses cells have been utilized in the attempt to separate male and female spermatozoa with applied potentials varying from 200 microvolts to 10 volts DC, the outcome has been disappointing particularly when the concentration of separated cells was too low to achieve a fair conception. The use of higher current while possibly increasing the purity of the separation has been found to lower the viability of the sperm. These problems have been substantially overcome in the present invention where sperm fractions containing substantially unbalanced populations of X and Y cells resulting from a first separation by thermal convection counter streaming sedimentation are placed in a forced convection column maintained between the two electrodes of an electrophoreses cell thus causing the respective cells of different charge to be preferentially drawn to their respective electrodes in a more efficient manner than heretofore obtained.

It has been noted in the past that the presence of foreign particles in the medium disturbs both the buoyant or sedimentation velocity of the sperm and their movement due to galvanic forces as well as their fertilization capacity after separation. The use of the universal medium disclosed in U.S. Pat. No. 3,816,249 substantially eliminates this problem while promoting control of cellular hyperactivity and prolonging sperm life as well. The use of the universal medium as well as the imposition of a low temperature immobilizing the sperm prevents the small difference in density (2 to 5%) and electric cell surface potential between male and female sperm from being neutralized by the high metabolic activity of the sperm cells.

SUMMARY OF THE INVENTION

In the present invention, positive and negative buoyant forces in combination with galvanic forces are used to achieve a more efficient separation of male and female sperm from a mixture of semen and particle-free medium. In the first part of the present method, the medium is held in a vertical sedimentation column under the influence of a thermal convection counter stream at low temperatures thus inducing separation of the differing sperm cells according to density. Subsequent to this separation step each of the lighter and heavier fractions, containing unbalanced sperm populations predominating in Y and X chromosome sperm, respectively, are separately processed in the forced convection galvanization apparatus by separately injecting each fraction into a central convection column located between the two arms of an electrophoreses cell containing, respectively, positive and negative electrodes. Galvanic potential is applied to the sperm cells while they are circulated in the column in a manner similar to the circulation achieved previously in the thermal convection counter stream. The forced convection circulation in combination with controlled conditions of temperature, ionic strength and pH of the medium, and voltage make possible separations of X and Y sperm cells to a purity of as much as 92% or more.

The first part of the present invention wherein X and Y sperm cells are separated according to differing density is based on the theory that in a closed vessel the molecules contained therein can be influenced to move in two counter streaming courses when a temperature differential is created between two adjacent areas. In a vertical column of fluid when the peripheral temperature is maintained lower than the axial temperature, a counter stream will be formed moving a peripheral portion of the liquid downwards and the axial portion upwards due to the difference in temperature. The rate of flow of these streams in either direction is dependent on the difference in densities created between the sections. Thus any change in the temperature differential will influence the densities and the rate of flow of the two streams.

If two classes of particles of different density and volumne are introduced into a constant counter current stream in a vertical column, the particles will initially be influenced by the velocities of the counter streams; then positive and negative buoyant forces acting on the particles will follow a definite physical law, carrying them apart.

According to the present invention a thermal convection counter stream is produced within the sedimentation column causing one portion of the medium therein to move at velocity V in an upwards direction and another portion of the medium to move with velocity V in a downwards direction. X-sperm and Y-sperm suspended within the medium will be caused to move at velocities $V_x$ and $V_y$, respectively, which velocities will be affected by the velocity of the medium V, the direction of the movement of the medium upwards or downwards, and gravity which will apply a different force on X-sperm particles than on Y-sperm particles according to the differing densities of the two types. As a result of these factors a Y-sperm particle which is less dense than an X-sperm particle tends to rise faster in that portion of the medium moving in an upwards direction and to settle slower in that portion of the medium moving in a downwards direction. Conversely, an X-sperm particle which is more dense tends to rise more slowly than a Y-sperm particle when the medium is moving in an upwards direction and tends to settle more quickly than the Y-sperm particle when the medium is moving in a downwards direction. Over a period of time these circumstances cause the less dense Y-sperm particles to accumulate near the top of the sedimentation column and the more dense X-sperm particles to accumulate near the bottom of the sedimentation column.

The convectional currents serve to aid and accelerate the process of separating the two classes of particles. Therefore, the minute density differential effect is used in conjunction with the convectional counter stream to obtain a purer and optimum separation of the two classes in a shorter time.

From the observational data, it has been noticed that the average velocity of the particles in pure sedimentation field at 5° C is 33 m.per second, whereas, the average velocity in convection counter stream is 120 m.per second. When the height of the column was selected at 18.2 cm, the average time taken for pure sedimentation amounts to 15.4 hours in contrast to 24.3 minutes when convection current was used.

In the second portion of the present invention, fractions of medium having unbalanced populations predominating in either X or Y chromosome containing sperm resulting from thermal convection counter streaming sedimentation are further separated and concentrated by convection galvanization taking advantage of the differing electric cell surface potentials of the X and Y chromosome containing sperm cells.

It has been generally agreed that both X and Y containing sperm possess a net negative charge at neutral pH (pH 7.0) and would thus both migrate towards the anode during electrophoreses. It has been found, however, that male or Y chromosome containing sperm have a more negative charge on the head than on the tail and are thus drawn toward the anode head first while female or X chromosome containing sperm are drawn toward the anode tail first due to a higher negative charge on the tail than on the head. Thus, active or motile sperm are found to be swimming in different directions during such electrophoreses with the male or Y chromosome containing sperm swimming in the direction of the anode, thus adding electrophoretic velocity to swimming velocity while the female or X chromosome containing sperm swim toward the cathode with their electrophoretic progress being opposed by their swimming progress. On the other hand, immobilized sperm such as those at a low temperature (e.g. 3°–5° C) contribute substantially little swimming velocity to their movement which is then determined mainly by their electrophoretic velocity found to be substantially equal in neutral buffer solutions, as mentioned above. It has been found, however, that X and Y chromosome bearing sperm can be made to differ in their net surface charges according to the type of buffer involved and the pH thereof. The separation of X and Y chromosome-containing sperm is thus dependent on the adjustment of the net surface charge of the respective X and Y cells which vary according to pH, ionic strength and concentration of divalent ions in the buffer, as well as temperature, current and voltage utilized in the electrophoretic cell. Although greater separation velocity in the electrophoretic cell may be expected if the sperm cells are motile, since they swim in opposite directions in practice it has been found that the characteristics of motile cells may alter quickly due to their activity. It has thus been found necessary for maximum efficiency of the separation as practiced in the present invention to immobilize the sperm cells immediately subsequent to ejaculation so as to prevent the cells from absorbing materials from the surrounding fluid or producing metabolic by-products, either one of which would substantially alter the pheno-typical differences which allow separation by net difference in electric potential as well as the separation described above according to differing density. It will thus be obvious that the use of the particle-free universal medium disclosed in U.S. Pat. No. 3,816,249 is significant in both aspects of the present invention in order to control the metabolism and hyperactivity of the sperm cells so as to allow phenotypical differences in density and electric cell potential to be utilized.

It has furthermore been found that the use of an unbalanced population in the convection galvanization step, that is the use of a fraction of medium containing substantially more of one type of sperm cell than the other type is of substantial significance to the degree of success of galvanic separation and concentration. The electrostatic state between the cells having a positive zeta potential (X chromosome or female sperm cells), the cells with negative zeta potential (Y chromosome or male sperm cells), and the medium dielectric constant is advantageously unbalanced in order to permit efficient separation in a galvanic field. The thermal convection counter streaming sedimentation process described above augments the galvanic separation step and supplies the unbalanced population condition necessary for most efficient separation by galvanic means.

It will be clear from the above that the combination of thermal convection counter streaming sedimentation and convection galvanization provides substantially more efficient separation of X and Y chromosome containing sperm than either the counter streaming sedimentation process or the galvanization process utilized separately. It should be noted at this point that while thermal convection counter streaming sedimentation is the preferred method for creating an unbalanced sperm population for use in the forced convection galvanization step of the present invention, various other methods of preliminary X and Y cell separation may be utilized in combination with the forced convection galvanization disclosed herein with varying degrees of success proportional to the degree of separation achieved by the first method utilized. Thermal convection counter streaming sedimentation has been found to be the most efficient of these methods of primary separation and is preferred in the present invention for combination with forced convection galvanization separation.

It should also be noted that the convection circulation which is produced during convection galvanization may be either forced convection circulation or thermal convection circulation. In the following specification it should be clear that thermal convection may be used instead of forced convection.

In one embodiment of the present method using forced convection galvanization, fractions of universal medium containing desired X and Y chromosome sperm ratios are injected into the central forced convection column and due to the narrower diameter of the top of the column utilized, a backflow in the opposite direction creates the forced convection circulation. Circulation of the medium has been found to aid in the galvanic separation of the unbalanced sperm population.

Alternatively to the above, a convection may be achieved in the galvanic cell convection column by producing a thermal gradient, substantially as described for the thermal convection produced in the sedimentation column. This would provide the desired convection circulation in the galvanic cell.

It is furthermore possible, as will be described, to combine the thermal convection counterstream sedimentation column and the forced convection galvanization cell in one apparatus and carry out both processes in the same column. In this embodiment, the thermal convection sedimentation would be performed until the desired separation by density was achieved, and then galvanic forces could be applied to the medium in the column, without any transfer to another apparatus. The thermal convection could be continued during galvanization as desired.

While any ionic buffer solution known in the prior art can be utilized in the forced convection galvanization method of the present invention, the universal medium as disclosed in U.S. Pat. No. 3,816,249 is preferably utilized as the sole medium in the forced convection galvanization cell. The universal medium, as previously disclosed, may have a pH of from about 6 to about 8, and an osmolality generally between 250 to 350 mos/kg. Preferably, universal medium composition will be utilized having a pH in the range of from about 6.8 to about 7.0 and an osmolality of approximately 300 mos/kg. It has been found that use of a slightly acid medium during forced convection galvanization is most preferable in that it accentuates the net cell surface potential differences between X and Y chromosome containing sperm.

The apparatus of the present invention utilized in one embodiment for forced convection galvanization comprises an electrophoreses cell having a central forced convection column and two arms of the cell communicating therewith containing the positive and negative electrodes, respectively. It is to be noted that while the prior art has experimented with electrophoretic or galvanic separation of X and Y sperm cells, the use of convection galvanization utilizing convection circulation of the sperm cells during galvanic separation, has not been used insofar as is known, prior to the present invention.

The present invention in addition to apparatus utilized for forced convection galvanization as described above includes apparatus for producing thermal convection counter streaming sedimentation, comprising means adjacent to a sedimentation column for producing the required temperature differential between two portions of the medium contained therein. Additionally, means are provided to determine the extent of accumulation of the two sperm populations at different levels within the sedimentation column both during and after thermal convection counter streaming. This may be achieved by several different means. Small fractions of the medium may be drained to determine the location and concentration of X-sperm and Y-sperm cells or a plurality of small hydrometers may be introduced into the sedimentation column to make the determination by measurement of density. Alternatively, the determination may be made by measurement of conductivity at various points within the column. In the preferred embodiment, the means for determining the location and concentration of the sedimented layers comprises a laser and laser detecting means in combination with means for scanning the laser beam throughout the length of the sedimentation column. Variations in the opacity of the medium to a particular wave length are thus determined, without the necessity of physically disturbing the contents of the sedimentation column in any way. This also facilitates the recording of variations in particle distribution and in the location and concentration of separated layers of X and Y-sperm cells.

Accordingly, it is an object of the present invention to provide a more efficient method for controlling the sex of mammalian offspring by obtaining a more complete separation of X-sperm and Y-sperm than has heretofore been possible.

Another object of the present invention is the provision of a method and apparatus for convection galvanization wherein galvanic potentials are utilized to separate X and Y chromosome containing sperm cells according to the differing electric potentials on the cell surfaces thereof while the sperm cells are being circulated in a convection column so as to create the unbalanced condition necessary for more efficient galvanic separation.

It is also an object of the present invention to provide a method for the separation of X sperm and Y sperm which takes advantage of the production of an unbalanced sperm population by thermal convection counter streaming sedimentation and utilizes this unbalanced population in a successful method of convection galvanic separation of the sperm cells so as to further separate and concentrate the unbalanced population resulting from such thermal convection counter streaming sedimentation.

A further object of the present invention is to provide a method of separating sperm according to phenotypical differences related to normal and abnormal genotypes by utilizing differences in their density and cell surface electrical potential.

Additional objects and advantages of the invention will appear from the following description in which the preferred embodiments have been set forth in detail in conjunction with the accompanying drawings in which:

DETAILED DESCRIPTION OF THE PREFERRED EMBODIMENTS

Figure 1:
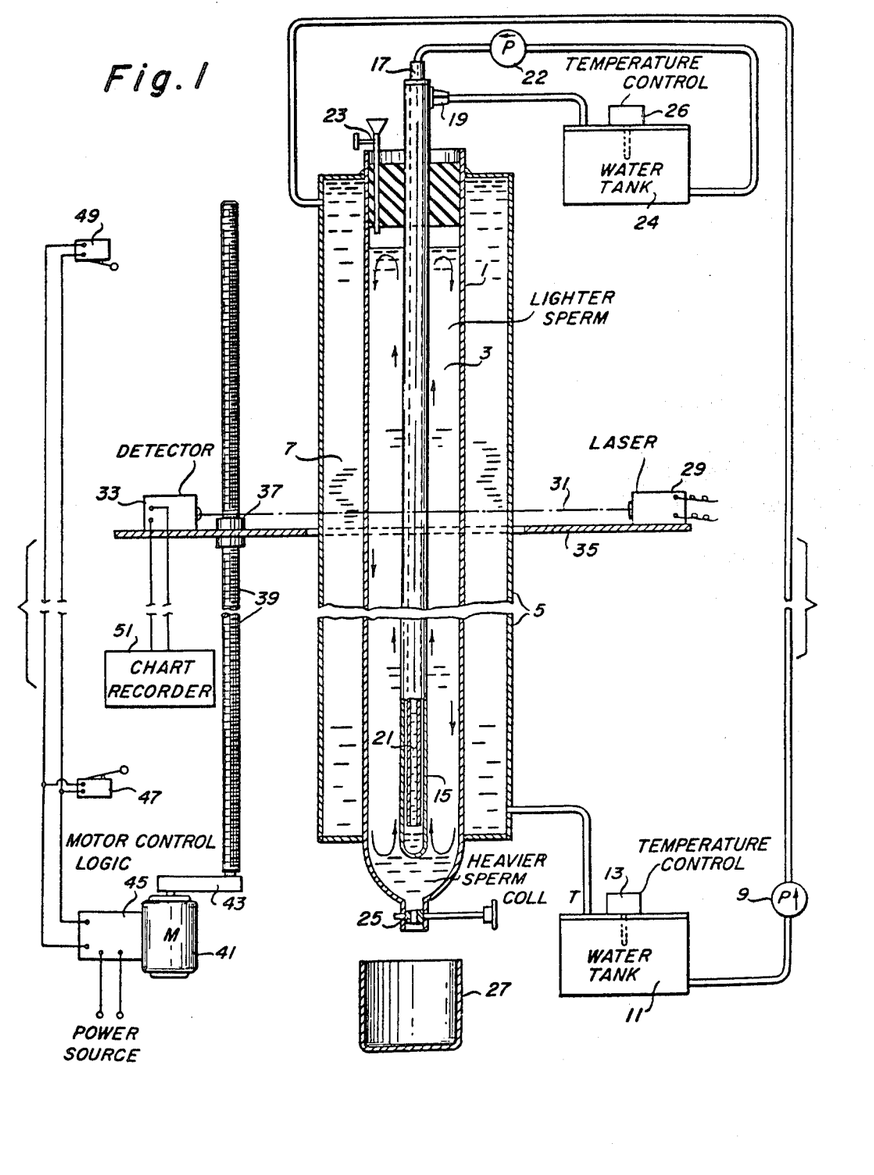
FIG. 1 is a diagram of a thermal convection counter streaming sedimentation apparatus which may be used in carrying out the first step of the present invention.

Shown in FIG. 1 is an illustration of the preferred embodiment of the apparatus used to carry out the first portion of the method of the present invention, that is, the thermal convection counter streaming sedimentation process. A sedimentation column 1 containing the universal medium 3 with both X-sperm and Y-sperm cells suspended therein is surrounded by a water jacket 5 through which a first water stream 7 of a first temperature is pumped by water pump 9. The water is drawn through water tank 11 where the temperature of the water can be controlled by temperature control means 13. This may comprise a cooling element with precise thermostatic control. Within the medium 3 is shown a second water jacket 15 which is coaxial with sedimentation column 1 and which has inlet 17 and outlet 19. A second stream of water 21 flows through water jacket 15 and may be pumped by means 22 through water tank 24 and its temperature controlled by separate means 26. In the event that the temperature of water stream 7 is the same as water stream 21 the entire medium within the sedimentation column will be at a uniform temperature. If a temperature differential is created between the two water streams, a thermal convection counter stream will result within the medium contained in the sedimentation column. It will be understood of course that other fluid heat exchange mediums may be used in lieu of water.

Inlet means 23 are provided for introducing sperm cells into the medium contained in the sedimentation column and outlet means 25 are provided for withdrawing fractions of sperm of substantially one chromosome type after sedimentation has been completed and collecting them in container 27.

In order to determine the progress of sedimentation as well as the location and concentration of the different types of sperm cells within the medium, means are provided for scanning the length of the sedimentation column and determining the relative opacity at different points therein. These means are described in detail in U.S. Pat. No. 3,976,197 which is incorporated herein by reference.

The apparatus thus described has the capability of efficiently producing the thermal convection counter stream of the method of the present invention as well as to efficiently determine the location and concentration of separated X and Y-sperm cells.

Figure 3:
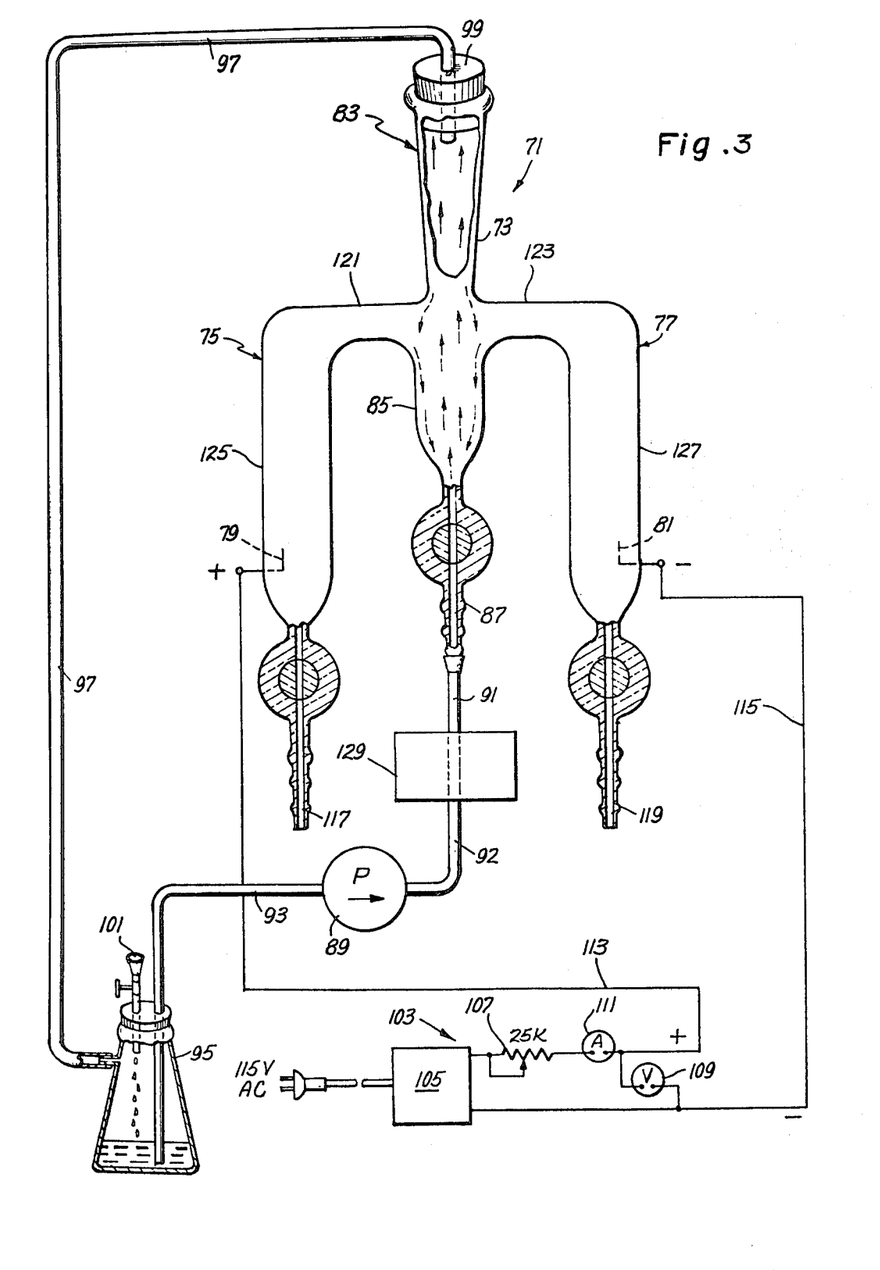
FIG. 3 is a diagram of apparatus which may be utilized in the forced convection galvanization step of the present invention.

Shown in FIG. 3 is an illustration of a preferred embodiment of convection galvanization apparatus used to carry out the second portion of the method of the present invention wherein the unbalanced sperm population fractions resulting from thermal convection counter streaming sedimentation are further separated and concentrated. While forced convection is utilized in the following description, it should be clear that thermal convection could be substituted therefor in the practice of the present invention.

Shown generally as 71 is a forced convection electrophoretic cell having a central forced convection column 73 with two bent tubes 75 and 77 communicating therewith and containing respectively positive and negative electrodes 79 and 81. It will be noted that these anode and cathode containing tubes communicate with the forced convection column on opposite sides thereof so as to maximize the movement of oppositely charged sperm cells under galvanic forces.

Convection tube 73 is comprised of an upper section designated as 83 and a lower section designated as 85 with the upper section being substantially narrower, 1 centimeter in diameter in the present embodiment than the lower section which is 1.5 centimeters in diameter in the present embodiment. The lower end of the convection tube has inlet means 87 for attachment to peristaltic pump 89 through tube 91, heat exchange means 129 and tube 92. The pump is connected through tube 93 to the outlet of semen reservoir 95 which may be an erlenmyer flask. The inlet of the semen reservoir is connected in turn to tube 97 which communicates with an outlet 99 at the upper end of convection tube 73. Semen reservoir 95 is furthermore provided with an inlet 101 for placement of a semen mixture containing an unbalanced sperm population of X and Y sperm cells therein. Heat exchange means 129 is provided in close proximity to inlet means 87. The temperature of the medium flowing through the cell may thus be controlled, so as to keep the sperm immobile and at a low metabolic rate.

In further association with electrophoretic cell 71 is a power supply generally designated at 103 which is comprised of a DC power source or rectifier 105 which may be plugged into any standard AC outlet, the DC output of which may be controlled by potentiometer 107 in order to produce any desired voltage as measured by voltmeter 109. An ampmeter 111 is also provided for the monitoring of current flowing through the electrophoretic cell by means of wires 113 and 115 connected to the anode and cathode, respectively, of said cell. Upon completion of forced convection galvanic separation of the X and Y chromosome containing sperm cells to the desired degree, the desired fractions are withdrawn through outlets 117 and 119 which communicate respectively with the tubes containing anode 79 and cathode 81. The fraction of medium drawn off through valve 117 from the arm of the cell containing anode 79 will contain substantially completely Y chromosome containing cells which are male producing and which have been drawn to the positive anode due to their net negative cell surface potential. The portion of the medium drawn off through outlet 119 communicating with the arm of the cell containing cathode 81 contains predominately X chromosome containing sperm cells which are female producing and have been drawn to the negative cathode due to their net positive cell surface potential.

It will be noted that those portions of the electrode containing arms of the cell shown at 121 and 123 are slightly less than one centimeter in diameter whereas the portions of the arms communicating with the electrodes shown at 125 and 127 are of a wider diameter, in this embodiment 1.5 centimeters. The degree of constriction at the horizontal portions of these arms, i.e. 121 and 123, as well as the slight constriction in the upper part of the convection tube at 83 relative to the lower part 85 has been found to aid in both the production of a convection circulation within the lower portion 85 of the convection tube and facilitate the tendency of Y and X chromosome containing sperm cells to be drawn into electrode tubes 75 and 77.

Figure 4:
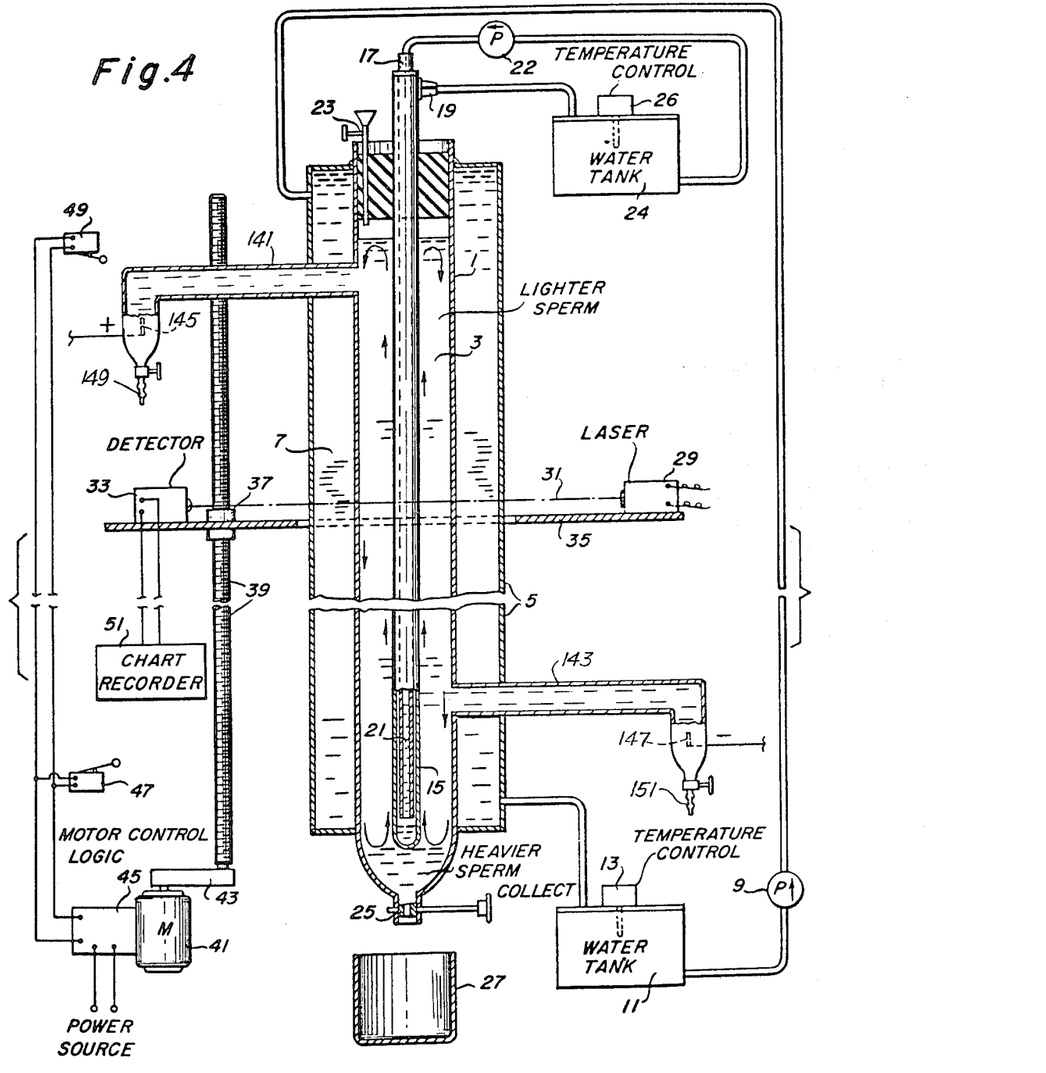
FIG. 4 is a diagram of an embodiment of the present invention combining the thermal convection counterstream sedimentation apparatus with the convection galvanization apparatus.

In an alternate embodiment of the present invention as shown in FIG. 4, the sedimentation apparatus and galvanization apparatus may be combined. In FIG. 4, all elements described previously relating to the thermal convection counter streaming apparatus may be identical to that shown in FIG. 1. The following additions to the apparatus are made, however.

The sedimentation column 1 has two bent glass tubes 141 and 143 communicating therewith at different vertical levels. These glass tubes contain respectively an anode 145 and a cathode 147 and each has respective outlet means 149 and 151. DC power may be supplied by means similar to those shown at 103 in FIG. 3. It will be clear in this embodiment that the sedimentation column 1 performs the function of convection column 73 in FIG. 3.

Figure 2:
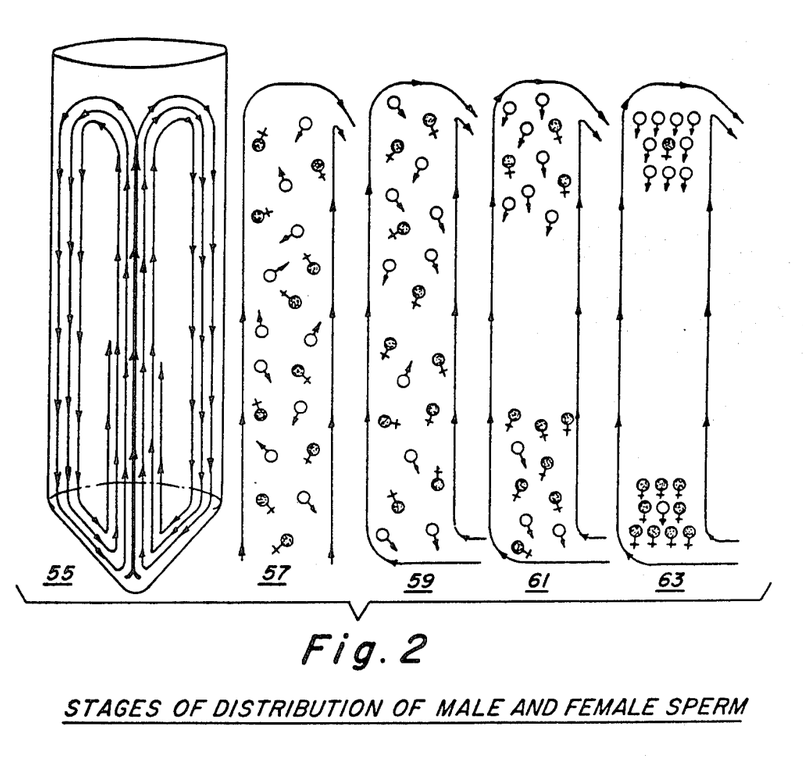
FIG. 2 is a representation of the operation of a sedimentation step useful in the process of the present invention.

The first portion of the method of the present invention as performed by the thermal convection counter streaming sedimentation apparatus first described above will now be described with reference to both FIGS. 1 and 2.

As discussed previously the preferred medium for use in the sedimentation column in the method of the present invention is the universal medium described in U.S. Pat. No. 3,816,249. This medium comprises a mixture of glycine, α-aminopropionic acid and egg yolk in amounts effective in aqueous solution to extend the life of said semen. The preferred composition of this medium comprises an aqueous solution having a pH in the range of from about 6.0 to 8.0, and containing, by weight, from about 0.01 percent to about 1.0 percent glycine, from about 0.01 percent to about 1.0 percent α-aminopropionic acid, from about 0.1 percent to about 2.0 percent of sodium chloride, potassium chloride or calcium chloride, from about 30 percent to about 55 percent egg yolk, and from about 30 percent to about 70 percent water and is filtered using millipore size 0.2μ filter. As noted previously, this universal medium has been found to be ideal for use in the forced convection galvanization apparatus described above as well as in the sedimentation step due to the ability to tailor both the pH of the medium as well as the osmolality to the degree required for most efficient galvanic separation of the sperm cells. The osmolality of the universal medium may range from about 250 to about 350 mos/kg. While this medium is preferred, it is possible to practice either the first or second portion of the method of the present invention with other particle-free mediums of appropriate composition and especially those of appropriate pH and ionic conductivity concentration for the galvanization portion of the present method.

Fresh sperm containing equal amounts of X and Y-sperm is collected from the male and mixed immediately with the universal medium at 22° C. The sperm mixture is then diluted further to 30 million cells per ml and checked microscopically for its quality. Only mixtures with excellent grading are used in the separation procedure.

The temperature of the sperm mixture is gradually lowered to 15° centigrade and then introduced into a sedimentation column, for example, the column 1 of FIG. 1. The outer water stream 7 (FIG. 1) is maintained at a temperature of 3.5° centigrade throughout the operation, and water stream 21 contained in coaxial water jacket 15 is maintained at 10° centigrade for one half hour and then brought down to 3.5° centigrade in another half hour by simply cutting off circulation within the coaxial tube. It should be understood that the above temperatures are only representative. In practice, the process may be carried out at any temperature which is sufficiently low to prevent the activity of the sperm cells from interfering with the sedimentation process. The temperature differential created as described above is also exemplary and any differential which would create sufficient convection counter streaming to facilitate sperm cell separation within a reasonable time would suffice. As previously discussed, the combination of this low temperature and the use of the particle free universal medium play an extremely important role in the invention by immobilizing the sperm so that they effectively become inert particles. This enables the subsequent positive and negative buoyant forces applied to use the 2% - 5% difference in density of the two types of sperm to effect a separation. During the period of temperature differential between the central and outer portions of the medium within the sedimentation column a thermal convection counter stream shown diagrammatically at 55 of FIG. 2 occurs which produces the positive buoyant force in this embodiment. Gravitational sedimentation is the negative buoyant force, and continues when the temperature differential becomes zero and the motion of the medium ceases. It takes ½ to 8 hours to achieve satisfactory separation beginning with introduction of the sperm mixture into the universal medium contained in the sedimentation column. Throughout this period, distribution of sperm in the sedimentation column at different times, shown at 57, 59, 61 and 63 of FIG. 2, is determined in a preferred embodiment by use of the laser scanning system described in detail in U.S. Pat. 3,976,197. As the convection separation is stopped, concentration of cells by sedimentation continues dragging both lighter and heavier sperm towards the bottom. By utilizing a chart recorder 51 connected to laser detecting means 33 the distribution of sperm at different times in the separation period can be recorded and observed. When the distribution is considered adequate, outlet means 25 can be opened and the fluid is allowed to drop into container 27 at a rate of approximately 20 drops per minute. The first fractions collected from the sedimentation column will contain the heavier X-chromosome containing sperm and successive fractions will contain less X-chromosome sperm and more Y-chromosome sperm until the final fractions collected will contain substantially all Y-chromosome sperm. At this point it is possible to centrifuge separately the lighter Y chromosome containing fraction and the heavier X chromosome fraction so as to concentrate and purify the products, and both the X and Y fractions may be utilized at this point for insemination. It is desirable, however, to further concentrate and purify the X and Y chromosome containing fractions by forced convection galvanization as described below.

Subsequent to the removal of the desired fraction of medium from the sedimentation apparatus containing an unbalanced X-chromosome/Y-chromosome sperm population, the fractions, which are preferably on the order of approximately 50 cc. are mixed with 150 cc of fresh medium at 3° to 5° C. This mixture is added to the erlenmyer flask 95 in FIG. 3 and peristaltic pump 89 is set at a very low rate forcing the fluid from the erlenmyer flask into the middle of the convection column through inlet means 87. The entire electrophoretic cell including sidearms 75 and 77 as well as convection column 73 have previously been filled with fresh medium at the desired temperature which is maintained by activating heat exchange means 129 and pump 89. As the semen containing universal medium is forced through inlet means 87 to the middle of the tube, the narrower portion of the convection column shown at 83 creates a backflow in the opposite direction facilitated by the wider portion of the tube shown at 85, thus creating a convection circulation as indicated by the arrows in the lower portion of convection tube 73. This convection carries oppositely charged spermatozoa by the opening of side tubes 75 and 77 containing respectively the anode and cathode of the electrophoretic cell. Power supply 105 is activated and potentiometer 107 is used to accurately set the desired voltage and current flow through the system. While the voltage utilized in the present invention may be anywhere in the range of from about 1 to about 5 volts with the current on the order of several hundred microamps, the preferred range is from about 2 to about 4 volts of galvanic force creating a current of from about 100 to about 400 microamps depending on the ionic concentration of the medium utilized. In practice the lower limit of voltage useful is that necessary to create substantial migration of the sperm cells towards their respective electrodes within an efficient amount of time, with the upper limit of voltage being that which will not permanently affect the motility or virility of the sperm cells. In one embodiment, a voltage of 2.3 volts was used with a resulting current of 200 microamps.

It should be noted that the circulating fluid in the system contains a relatively low concentration of sperm (i.e. 15 million per cc) which low concentration prevents the clumping of the spermatozoa which are moving in the opposite direction to the galvanic field.

Upon the application and adjustment of voltage to electrodes 79 and 81, the circulating sperm cells in the convection column are subjected to galvanic forces. These galvanic forces are accentuated by the utilization of a medium in the electrophoretic cell having a pH and ionic concentration of the proper values. While mediums of a pH of from about 6.0 to about 8.0 may be utilized in the present invention, it has been found that the net electrical potential difference on the respective cell surfaces of X chromosome and Y chromosome containing sperm is accentuated in a medium of pH from about 6.8 to about 7.0. As noted, the ionic concentration or osmolality of the medium is also of significance in the present proccess and while compositions with osmolalities ranging from about 200 to about 400 mos./kg., or an even greater range may be utilized, values of from 250 to 350 mos/kg are preferred and the osmolality found to be useful in the present embodiment was about 300 mos/kg.

During forced convection galvanization, the escaping hydrogen and oxygen from the respective electrodes is trapped at the top of bent side tubes 75 and 77 where the gases can easily escape and mix with the circulating fluid. This is a distinctive advantage over other cells where nascent hydrogen and oxygen may injure the spermatozoa.

The slow circulation of medium through the electrophoretic cell as described above is maintained until the desired degree of separation is achieved, which under the circumstances of the present embodiment, may be, for about 30 minutes for each fraction processed. After separation is completed to the desired degree, circulation is stopped and power to the electrodes disconnected. The desired male and female medium fractions are drawn off from the two electrode tubes through outlets 117 and 119 with the amount of medium drawn off being carefully regulated so as to prevent substantial amounts of the medium which had still been circulating in the central convection tube from being drawn off. Subsequently, the fluid from the central column may be forced back into the flask. Alternatively to the above, the fluid from the central portion of the column may first be drawn off into the erlenmyer flask, it being necessary in this case to ensure that all separated sperm population has been drawn towards the electrodes past the bent arms of side tubes 75 and 77 so that when the medium is drained from the central column, that portion of the medium flowing out of side tube sections 121 and 123 does not contain substantial amounts of separated sperm populations which would be mixed upon flowing back into the central convection column. The fractions in the lower portions of side arms, that is portions 125 and 127, may then be drawn off through outlets 117 and 119.

In the event that the combined sedimentation and galvanization apparatus shown in FIG. 4 is utilized, a procedure similar to that described above is followed, without the steps of transferring the sperm cells from one apparatus to the other.

After thermal convection counter streaming sedimentation is completed, the circulation is slowed and galvanic forces are applied to electrodes 145 and 147 in FIG. 4. A predominately Y chromosome containing population has accumulated near the top of the sedimentation column, which sperm have a net negative cell surface electrical potential, and are thus further concentrated by attraction into side tube 141 towards positive anode 145. A similar population predominating in X sperm which have a net positive charge is present near the bottom of the column and is further concentrated by attraction into side tube 143 towards cathode 147. The desired fractions may then be drawn off through outlets 149 and 151, respectively.

While the separated fractions may be processed as desired, the following method is preferably used.

Equal amounts of universal medium (containing about 20% glycerol) is used to dilute the fractions drawn off from outlets 117 and 119 to the desired volume and sperm cell number which is preferably approximately 20 million cells per ml. and the mixtures are then held at 5° to 8° C for 4 to 6 hours in order to equilibrate the glycerol with the cells. The material may then be put into one ml. ampules, sealed, marked as male or female or mixture in the event of the fraction drawn off from the central convection tube, frozen and stored in liquid nitrogen.

The purity of male and female fractions obtained by the method outlined above may be tested either serologically by producing antibodies or may be checked by the B-body or F-body tests. It should be pointed out that sperm fractions resulting directly from any of the above described embodiments or combinations thereof may be processed as follows. The lighter and heavier fractions from the sedimentation column or the anode and cathode fractions from the forced convection galvanization apparatus are centrifuged repeatedly with fresh medium in order to concentrate and purify the different sperm types. The sediment in the heavier fractions and the supernatant in the lighter fractions subsequent to repeated centrifuging and washing are considered to hold the most pure forms of the female and male sperm respectively. The subsequent procedure for serological testing is followed as described in my U.S. Pat. No. 3,692,897, column 3, lines 11 through 43 and column 5, lines 5 through 55.

Alternatively to the above, the purity of the separated and/or non-separated semen may be checked with the B-body test. This test is based on the knowledge that Y spermatozoa of humans and primates tends to fluoresce with a special brightness when stained with quinacrine-HCL or quinacrine-mustard with the staining technique being simple and generally accepted by the prior art. While attempts have been made in the past to extend this technique in order to identify male and female spermatozoa in other domestic animals besides humans and primates, failure has been reported in many instances. My analysis on the subject encouraged me to develop a successful technique of staining Y spermatozoa by this method in other species since human and primate sperm contain a large quantity of proteolotic enzymes which partially dissolve the sialic acid-protein complex, glyco- and lypo-protein coating of the sperm membrane, which has been found to enhance the penetration of the dye into the chromatin materials. Thus, after the utilization of different enzymes at different concentrations, temperatures, and pH's, etc., I have particularly found that papaya protease (available Sigma Chemicals, U.S.A.) is suitable for the purpose of performing a similar function artificially on the cell membranes of the sperm of other domestic animals.

The above process is carried out as follows: Approximately 1 milliliter of semen or medium mixture (containing from about 20 million to 50 million cells) is washed with saline and may be centrifuged three times at 2,500 grams for 15 minutes. This centrifuging and washing, if it is in addition to that first described above, may be optional. After diluting the sediment with 1 milliliter of fresh saline in the present example, 3 drops of this suspension is mixed with 5 miligrams of protease and allowed to digest for approximately 10 minutes at room temperature. Subsequently, one drop of 0.005% quinacrine-mustard is added to 1 drop of the digested mixture, put on a slide, and mounted immediately for microscopic examination. After allowing 40 minutes for the dye to enter the inner structure of the spermatozoa, which is facilitated by the digestion of the outer membrane by protease, the spermatozoa may be viewed with a Leitz Ortholux microscope using the KP-490 Eciter Filter at a transmission wave length of 530 nanometers with two heat barriers, HP 430 and HP 460. Human spermatozoa treated in the above manner may take a deep stain without identifying Y chromosome containing sperm; however, bull and horse spermatozoa with the Y chromosome show a distinct bright spot with excellent visibility (B-body) with the X bearing spermatozoa taking a dull and diffused stain. Nonprocessed bull, human and horse semen and processed bull semen have been checked for B-bodies as a routine procedure for checking product purity in the practice of the present invention. The results in 523 experiments are tabulated below in Table I where the results from B-body tests are compared with that from biological tests.

TABLE I

A Comparative Study of the Product Purity (Female Fraction) in Relation to B-Body and Biological Test

| B-Body Tests | No. of Tests | Cells Counted | % Male | % Female |
|---|---|---|---|---|
| 1. Non-processed | 16 | 5,242 | 48.5 | 51.5 |
| 2. Convention Counter-Streaming Sedimentation | 65 | 26,000 | 40.9 | 59.1 |
| 3. Convection Counter-Streaming Sedimentation and Galvanization Biological Test | 28 | 11,200 | 30.3 | 69.7 |
| 4. Convection Counter-Streaming Sedimentation | 414 | | 43.5 | 56.5 |

It will be noted that the combination of convection counter streaming sedimentation with convection galvanization as shown in line 3 provides a substantial increase in product purity over convection counter streaming sedimentation when performed alone.

It should be noted that the specified enzyme concentrations, digestion and staining times, etc., as described above, are variable for individual bulls as well as horses. It is to be noted once again that the use of the protease enzyme in the digestion of the cell membrane is not necessary in many cases with human and primate cells due to the difference in the cell membranes thereof which enhances penetration of the dye without membrane treatment. The use of the enzymes is particularly suited to other domestic animals such as horses and bulls in order to enhance penetration of the dye through cell membranes.

In several cases in which the above process of thermal convection counter streaming sedimentation combined with forced convection galvanization was performed, samples containing as high as 92% X or Y chromosome containing sperm, with in some cases as many as 25 million viable sperm subsequent to thawing of the samples, have been achieved.

50 ampules of good-quality, high purity female semen processed as described in the manner of the present invention have been used for biological tests, that is, by insemination and conception and the samples have shown a very high conception rate.

Another method of identifying male sperm of human and primates is the F-body test which is based on the fact that one arm of the Y chromosome in summatic cells tends to fluoresce with quinicrine dye. Unprocessed human ejaculations treated with the F-body staining procedure have been found to produce almost half of the population fluoresing. While a biological test is impossible with humans, an obvious conclusion to be drawn is that the fluoresing population is synonymous to the fluoresing symmatic Y chromosome and hence the fluoresing cells are Y chromosome containing or male producing cells. The reproducibility of the F-body technique has been verified and is accepted now as a standard technique to identify male spermatozoa in human semen.

In order to evaluate the comparative efficiencies of F-body and B-body techniques, a comparative study has been made mixing human and bull semen and applying both F-body and B-body techniques for a positive and negative correlation. In particular, it has been found that the B-body test with bull semen fitted in very well with the biological test results.

In this comparison, 2 milliliters of human semen and 2 milliliters of bull semen were mixed and processed in this case by forced convection galvanic separation alone without the first described method of thermal convection counter streaming sedimentation. Subsequent to forced convection galvanic separation and processing as described above, the frozen male and female fractions containing bull and human semen were treated with the B-body and F-body tests respectively, with the following results being recorded.

TABLE II

Comparison of F-Body and B-Body Test Results

|  |  | B-Body Test | | F-Body Test | |
|---|---|---|---|---|---|
|  |  | % Male | Cells Counter | % Male | Cells Counted |
| Bull | N.P.* | 55.8 | 446 | — | — |
|  | Male | 57.6 | 1425 | — | — |
|  | Female | 40.5 | 646 | — | — |
| Human | N.P.* | 52.2 | 221 | 49.0 | 200 |
|  | Male | 59.4 | 223 | 53.5 | 200 |
|  | Female | 34.9 | 245 | 32.8 | 280 |

*Non-processed

It will be noted that the F-Body Test did not differentiate male and female bull spermatozoa.

It should also be noted that subsequent to the mixing of the human and bull semen and processing, identification of separate bull and human spermatozoa was still possible due to the different characteristics thereof.

The above results would indicate that firstly, the F-body test results in connection with human spermatozoa find general correlation with the B-body test results also performed on human spermatozoa, and secondly that the B-body test results performed on bull sperm finds general correlation with the B-body test results performed on human sperm. It may thus be concluded that the B-body test performed in connection with bull sperm is similar to the F-body test performed on human sperm. The B-body test (found to be easier and less complicated) is thus equally good for bull as well as for human male spermatozoa identification.

In one instance, a biological test was performed utilizing a group of cows artificially inseminated with female sperm derived by the first portion of the method of the present invention, that is, the thermal convection counter streaming sedimentation process as described first above. After 50 to 60 days of gestation, 9 of the cows were slaughtered and the observed fetuses were all of the female sex, thus indicating the substantial utility of thermal convection counter streaming sedimentation utilized alone.

It is feasible by using thermal convection counter streaming sedimentation as described first above as well as convection galvanization or a combination of both, to avoid most heavy and light sperm or sperm of abnormal phenotypical characteristics which are considered to form only a small fraction of the sperm population carrying abnormal chromosomes which may cause birth defects. This would reduce those cases of Klinefelter's and Turner's syndromes, and autosomal defects caused by nondisjunction and translocation of chromosomes, this being possible by the rejection of defective heavier and lighter sperm or sperm of unusual phenotypical characteristics related to the electrical potential on the cell surfaces thereof. As noted previously, this electrical potential difference on the cell surface is directly related to the chromosome structure in each cell and thus by careful classification of sperm according to such electrical potential differences, unusual or abnormal chromosomes may be easily discovered and rejected.

From the foregoing, it will be apparent that thermal convection counter streaming sedimentation combined with convection galvanization in the method of the present invention has utility whenever it is desired to control the sex of mammalian offspring. The combination of the above methods as well as either thermal convection counter streaming sedimentation or forced convection galvanization utilized separately are of extreme practical and commercial importance in order to meet the great demand in increasing herds, cattle and hog herds particularly, by selecting female offspring. This permits the breeder or farmer to have a choice of a sex in the animal. By way of illustration, the dairy farmer and exotic cattle breeder can elect to obtain only female offspring and thereby advantageously breed only milk producing cows rather than bulls, or on the other hand, exotic breed bulls rather than cows, as the case may be. As respects to human procreation, the present method and apparatus may allow normal parents to select or control the sex of offspring to quickly satisfy the desire to have a child of a particular sex, thus providing the opportunity to reduce the total number of children. The observed high fertility of sperm cells resulting from the process of the present invention will help in general to achieve success in artificial insemination. In the cases of parents carrying defective genes, the present method provides a sure and definitive manner of providing them with the opportunity of increasing the chance of having a normal baby by eliminating defective sperm having phenotypical characteristics of density and electric cell surface potential out of the norm.

What is claimed is:

1. A method of separating sperm cells of differing densities and electrical potentials from semen comprising the steps of:
   mixing semen with a liquid suspending medium;
   immobilizing the sperm by cooling the mixture;
   applying both positive and negative buoyant forces to the sperm whereby more dense sperm attain a different level in the liquid medium than less dense sperm;
   applying galvanic force to said medium while circulating said medium by convection so as to separate sperm having different net electrical cell surface potentials; and
   withdrawing a fraction of the medium containing the desired sperm.

2. A method as recited in claim 1 wherein said circulation by convection is produced by causing a forced convection circulation of said medium.

3. A method as recited in claim 1 wherein said circulation by convection is produced by causing a thermal convection circulation in said medium.

4. A method as recited in claim 1 wherein said more dense sperm are X-chromosome containing sperm, and said less dense sperm are Y-chromosome containing sperm, and said sperm of different electric cell surface potentials correspond to those sperm of a different chromosomal type.

5. A method as recited in claim 1 further comprising the step of allowing the sperm to further separate by gravitational sedimentation after the liquid medium is at rest.

6. A method as recited in claim 1 further comprising the step of applying the positive and negative buoyant forces by creating a temperature differential between portions of the mixture of sperm and medium in order to circulate the sperm by thermally produced convection counter stream.

7. A method as recited in claim 1 further comprising the step of centrifuging the fraction withdrawn to further purify the desired sperm.

8. A method as recited in claim 1 wherein said medium comprises a mixture of glycine, alpha-aminopropionic acid and egg yolk in amounts effective in aqueous solution to extend the life of said sperm.

9. A method as recited in claim 1 further comprising the step of determining the ratio of X chromosome sperm to Y chromosome sperm present in said withdrawn fraction of medium by subjecting said fraction of medium to a B-body test.

10. A method as recited in claim 1 further comprising the steps of:
staining any Y chromosome containing sperm cells present in said withdrawn fraction of medium with a compound selected from the group consisting of quinacrine HC1 and quinacrine-mustard; and
determining the proportion of sperm cells contained in said withdrawn fraction of medium which are stained relative to those sperm cells which are not.

11. A method as recited in claim 10 further comprising the step of treating sperm cells contained in said withdrawn fraction of medium with an enzyme capable of enhancing the penetration of said staining compound into the sperm cells.

12. A method as recited in claim 11 wherein said enzyme is papaya protease.

13. A method of separating mammalian sperm according to phenotypical differences related to normal and abnormal genotypes comprising the steps of:
mixing fresh semen with a liquid suspending medium;
separating the mixture by thermal convection counter streaming sedimentation according to different sperm densities into three fractions, a first fraction containing predominately X-sperm of a normal genotype, a second fraction containing predominately Y-sperm of a normal genotype, and a third fraction containing both X and Y-sperm carrying defective genes; and
subjecting a desired fraction of said medium to convection galvanization thus further separating and concentrating all X-sperm of a normal genotype and all Y-sperm of normal genotype.

14. A method as recited in claim 13 wherein said sperm are human sperm.

15. A method as recited in claim 13 further comprising the steps of:
mixing at least one separated fraction with a solution of from 5 percent to 20 percent glycerol; and
freezing the mixture in liquid nitrogen.

16. A method of separating sperm cells of differing cell surface electrical potentials from semen comprising the steps of:
mixing the semen with a liquid suspending medium;
applying galvanic force to said medium while subjecting it to convection circulation whereby sperm of one net cell surface electrical potential attain a different position within said medium than sperm of a differing net cell surface electrical potential; and
withdrawing a fraction of the medium containing the desired sperm type.

17. A method as recited in claim 16 further comprising the step of subjecting said mixture of semen and liquid suspending medium to a separation process which creates an unbalanced X-chromosome/Y-chromosome population ratio within said liquid suspending medium prior to the application of said galvanic force.

18. A method as recited in claim 16 wherein said convection circulation is produced by causing forced convection circulation of the medium.

19. A method as recited in claim 16 wherein said convection circulation is produced by causing a thermal convection circulation within said medium.

20. A method as recited in claim 16 further comprising the step of determining the ratio of X chromosome sperm to Y chromosome sperm present in said withdrawn fraction of medium by subjecting said fraction of medium to a B-body test.

21. A method of controlling the sex of mammalian offspring comprising the steps of:
mixing fresh sperm with a liquid suspending medium;
subjecting said mixture to thermal convection counter streaming sedimentation to separate according to differing densities sperm having X-chromosomes from sperm having Y-chromosomes;
removing a desired fraction of said mixture from said sedimentation column;
subjecting the desired fraction of said mixture to forced convection galvanization to further separate and concentrate according to different cell electrical potentials substantially all sperm having X-chromosomes from all sperm having Y-chromosomes; and
introducing the desired fraction into a female whereby conception occurs and offspring of the desired sex are produced.

* * * * *